United States Patent [19]

Schmidt

[11] 3,975,373

[45] Aug. 17, 1976

[54] CARDIOGLYCOSIDE DERIVATIVES OF THE STROPHANTHIDIN TYPE, A PROCESS FOR THEIR MANUFACTURE AND MEDICINAL PREPARATIONS CONTAINING THESE COMPOUNDS

[75] Inventor: Kurt H. Schmidt, Hildesheim, Germany

[73] Assignee: Johann A. Wülfing Fabrik Pharmazeutischer Präparate, Dusseldorf, Germany

[22] Filed: June 12, 1975

[21] Appl. No.: 586,174

Related U.S. Application Data

[60] Division of Ser. No. 170,635, Aug. 10, 1971, Pat. No. 3,951,946, which is a continuation-in-part of Ser. No. 810,946, March 27, 1969, abandoned.

[30] Foreign Application Priority Data

| Mar. 27, 1968 | Germany | 1768054 |
| Apr. 4, 1968 | Germany | 1768140 |
| Apr. 4, 1968 | Germany | 1768142 |
| Apr. 4, 1968 | Germany | 1768143 |
| Mar. 12, 1969 | Germany | 1912518 |

[52] U.S. Cl. .................................. 536/7; 424/182
[51] Int. Cl.² .................................... C07J 19/00
[58] Field of Search .............................. 260/210.5

[56] References Cited

UNITED STATES PATENTS

| 3,476,742 | 11/1969 | Voigtlander et al. | 260/210.5 |
| 3,781,269 | 12/1973 | Haede et al. | 260/210.5 |

*Primary Examiner*—Johnnie R. Brown
*Assistant Examiner*—Cary Owens
*Attorney, Agent, or Firm*—Kenyon & Kenyon

[57] ABSTRACT

Cyclic acetals or ketals of cardioglycosides derived from k-strophanthidin or strophanthidol are more readily absorbed by the stomach and intestine than the parent cardioglycoside. The acetals are produced by reaction of the parent cardioglycoside, e.g., strophanthidindigitoxide, with an aldehyde or ketone, or the corresponding acetal or ketal, in the presence of an acid condensation catalyst, to produce the k-strophanthidin derivative optionally followed by reduction to the strophanthidiol derivative.

1 Claim, No Drawings

CARDIOGLYCOSIDE DERIVATIVES OF THE STROPHANTHIDIN TYPE, A PROCESS FOR THEIR MANUFACTURE AND MEDICINAL PREPARATIONS CONTAINING THESE COMPOUNDS

RELATED APPLICATIONS

This is a division, of application Ser. No. 170,635, filed Aug. 10, 1971, and now U.S. Pat. No. 3,951,946, which is a continuation-in-part of application Ser. No. 810,946, filed Mar. 27, 1969, and now abandoned.

Cardioglycosides derives from k-strophanthidin or strophanthidol, for example, convallatoxin, convallatoxol, k-strophanthin, cymarin, cymarol, helveticoside and helveticosol, have a special importance in heart therapy, on account of the particular effectiveness of compounds with this type of structure. Their application, however, is virtually restricted to injection, since these glycosides are only very slightly absorbed from the stomach or intestine. For example, the enteral absorption rates of cymarin and helveticoside are 0% and 20 to 30%, respectively. These compounds, therefore, have an insufficient therapeutic efficiency in enteral application.

There have been numerous attempts either to find more readily absorbed cardioglycosides of the strophanthidin type or to improve the absorption by chemical changes in the molecules, for example, by the acylation of the hydroxyl groups. Until now, however, no glycoside has been known with properties which fulfill the therapeutic requirements, cf. Arzneimittererschung Vol. 13 (1963), pp. 142–149, and Dutch Patent Application 67 020 85 published Aug. 14, 1967.

It is an object of this invention to provide a new class of cardioglycosides which can be readily absorbed by the stomach and intestine and which cause only slight side effects. It is a further object of this invention to provide new processes for preparing a new class of cardioglycosides. Furthermore, it is an object of this invention to provide pharmaceutical compositions for oral and parenteral application which contain at least one cardioglycoside of the invention.

It is a further object of this invention to provide a method of treating patients suffering from cardiac disease.

Further objects will become apparent in the following description.

The new cardioglycosides of the invention have the general formula I wherein R denotes the formyl (CHO) or methylol ($CH_2OH$) group, $R_1$ denotes a hydrogen atom or a saturated or olefinically unsaturated straight or branched alkyl group with 1 to 10 carbon atoms, $R_2$ denotes a phenylalkyl group containing 1 to 4 carbon atoms in the alkyl moiety, the alkyl part of which can also be olefinically unsaturated or branched, or a phenyl group which may be substituted by 1 to 3 alkyl or alkoxy groups containing 1 to 4 carbon atoms or a methylenedioxy group, or $R_1$ and $R_2$ can form together with the carbon atom to which they are linked a cycloaliphatic residue containing 5 to 12 carbon atoms in the ring which may be substituted by 1 or 2 alkyl or cycloalkyl groups containing 1 to 6 carbon atoms. This invention also relates to new cardioglycosides wherein R is as defined above, $R_1$ denotes a saturated or olefinically unsaturated straight or branched alkyl group of up to 10 carbons and $R_2$ denotes a hydrogen atom or a saturated or olefinically unsaturated straight or branched alkyl group of up to 10 carbons, there being at least 8 carbons in the residue

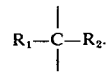

It is evident that the novel cardioglycosides of the general formula I are cyclic acetals or ketals, the residue

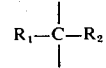

being derived from an aldehyde or ketone of the general formula IV stated further below.

Specific examples of particularly preferred cardioglycosides of the invention are benzaldehyde-helveticoside, acetophenone-helveticoside, cyclohexanone-helveticoside, cinnamaldehyde-helveticoside, cyclopentanone-helveticoside and cycloheptanone-helveticoside and the corresponding helveticosols ($R = CH_2OH$).

The names of the cardioglycosides of the invention as stated above and in the examples were chosen for the sake of clarity; they are not in accordance with the IUPAC nomenclature of organic chemistry. Thus, the correct name of e.g., benzaldehyde-helveticoside according to the IUPAC nomenclature would be 3',4'-benzylidene-helveticoside.

The cardioglycosides of the general formula I may be prepared by reacting the helveticoside, i.e., strophanthidindigitoxoside of the general formula II

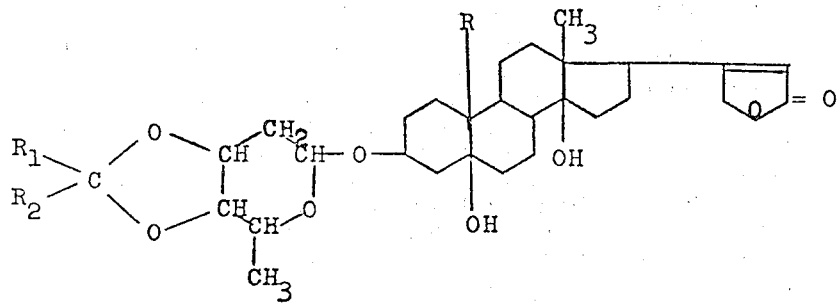

(I)

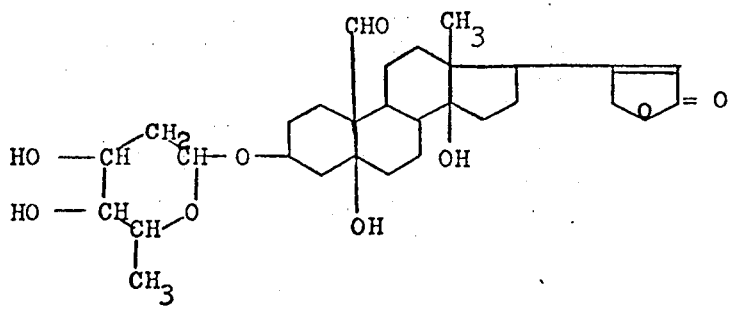

in the presence of a suitable acidic condensing agent with an acetal or ketal of the general formula III

wherein $R_1$ and $R_2$ have the above meanings and $R_3$ is an alkyl group containing 1 to 4 carbon atoms, to produce the cyclic acetal or ketal of the general formula I wherein R is the formyl group, or helveticoside, which optionally can be reduced with a suitable reducing agent to form the corresponding helveticosol (R = $CH_2OH$).

The cardioglycosides of the general formula I may also be prepared by reacting the helveticoside of the general formula II in the presence of a suitable acidic condensing agent with the corresponding free aldehyde or ketone of the general formula IV

wherein $R_1$ and $R_2$ have the above meanings to produce a helveticoside within the general formula I, which optionally can be reduced with a suitable reducing agent to the corresponding helveticosol (R = $CH_2OH$).

The acetal or ketal used in the invention process is derived from the corresponding aldehyde or ketone of the general formula IV. Preferably, the methyl or ethyl acetals and the methyl or ethyl ketals are used.

Examples of aliphatic saturated or olefinically unsaturated straight or branched aldehydes are:

n-heptyl aldehyde, n-nonyl aldehyde, n-decyl aldehyde, 3,3,5-trimethyl caproic aldehyde, 2-ethyl caproic aldehyde.

Examples of suitable aromatic aldehydes are:

benzaldehyde, o-, m-, and p-tolylaldehyde, mesityl aldehyde, p-isoprophybenzaldehyde, 2-, 3- or 4-methoxybenzaldehyde, piperonal, dimethoxybenzaldehydes, e.g. 3,4-dimethoxybenzaldehyde, and trimethoxybenzaldehyde.

Examples of aliphatic saturated or olefinically unsaturated aldehydes substituted by a phenyl group, which may also be substituted in the side-chain or in the benzene ring are:

phenylacetaldehyde, α-methylphenylacetaldehyde, dihydrocinnamaldehyde, p-methylphenylacetaldehyde, cinnamaldehyde, α-amylcinnamaldehyde, β-(p-isopropylphenyl)-α-methylpropionaldehyde.

Examples of aliphatic saturated or olefinically unsaturated straight or branched ketones are:

3-ethylpentanone-(2), propyl butyl ketone, ethyl n-amyl ketone, methyl decyl ketone, 2-methyl-7-ethylnonanone-(4), 2,6, 8-trimethylnonanone-(4), di-n-hexyl ketone, n-amyl n-heptyl ketone, butyl octyl ketone, ethyl decyl ketone, propyl decyl ketone, diheptyl ketone, 6-methyl-5-heptenone-(2), propyl isoamyl ketone, methyl hexyl ketone, propyl isobutyl ketone, butyl isopropyl ketone, ethyl isoamyl ketone, 5-methyl heptanone-(3), 3-methylheptanone-(2), dibutyl ketone, propyl n-amyl ketone, ethyl hexyl ketone, methyl heptyl ketone, isopropyl n-amyl ketone, di-isobutyl ketone, isopentyl isopropyl ketone, di-tert.-butyl ketone, propyl hexyl ketone, ethyl heptyl ketone, methyl octyl ketone, 3-methylnonanone-(2), isopropyl hexyl ketone, diamyl ketone, butyl hexyl ketone, propyl heptyl ketone, ethyl octyl ketone, methyl nonyl ketone, 3-butylheptanone-(2), di-isoamyl ketone, butyl heptyl ketone, propyl octyl ketone, and ethyl nonyl ketone.

Examples of aromatic or araliphatic ketones are:

acetophenone, 2-, 3-, or 4-methylacetophenone, 4-tert.-butyl acetophenone, 2,4,5-trimethylacetophenone, 2,4,6-trimethylacetophenone, 2-methoxyacetophenone, 4-methoxyacetophenone, 2,4-dimethoxyacetophenone, 2,5-dimethoxyacetophenone, propiophenone, 2-, 3- or 4-methylpropiophenone, 4-methoxypropiophenone, 2,4-dimethoxypropiophenone, butyrophenone, valerophenone, caprophenone, isopropyl phenyl ketone, isoamyl phenyl ketone, methylbenzyl ketone, ethyl benzyl ketone, propyl benzyl ketone, isopropyl benzyl ketone, dibenzyl ketone, benzophenone, benzylacetone, phenylethyl ethyl ketone, and phenylethyl propyl ketone.

Examples of cycloaliphatic unsubstituted or substituted ketones are:

cyclopentanone and its alkyl derivates, such as 3-methyl cyclopentanone and 3,4-dimethyl cyclopentanone; cyclohexanone and its alkyl derivatives, such as 2-, 3-, and 4-methylcyclohexanone; 4-ethyl and 4-tert.-butyl cyclohexanone; 3,5,5-trimethyl cyclohexanone (=dihydroisophorone); menthone; cycloheptanone and its alkyl derivatives; cyclooctanone; cyclononanone; cyclodecanone; cyclododecanone; camphor; and bicyclo-[2,2,1]-heptane-1-one (Norcamphor).

In the process for preparing the compounds of the general formula I acids, such as hydrochloric acid, sulfuric acid, potassium hydrogen sulfate, anhydrous Lewis acids, such as ferric chloride, zinc chloride or boron trifluoride etherate or anhydrous cupric sulfate can be used as condensing agents. The preferred condensing agent is a cation exchanger in the acidic form ($H^+$-form), which is inert in the temperature range of the reaction and under the other reaction conditions. As cation exchangers both inorganic and organic exchangers can be used. Organic exchangers are preferred. The exchangers are converted into the acidic form by treatment e.g. with an inorganic strong acid, subsequently washed with an organic solvent to remove the water and finally dried. After completion of the reaction, the reaction mixture is separated from the exchanger. In this way an additional neutralization stage is avoided which could otherwise lead to uncontrollable side-reactions. The condensing agent is used in at least catalytical amounts.

The method using an acetal or ketal of the general formula III and a cation exchange resin in the acidic form is especially preferred due to its wider field of application, the shorter reaction times, larger yields and less formation of by-products. This novel is of use in preparing a broader class of compounds of the general formula V.

formula VI are the acetals and ketals of aliphatic, saturated or olefinically unsaturated straight or branched aldehydes such as:

formaldehyde, acetaldehyde, propionaldehyde, n-butyraldehyde, n-valeric aldehyde, n-caproic aldehyde, iso-butyraldehyde, iso-valeric aldehyde, pivaldehyde, 2-methyl-n-valeric aldehyde, 2-ethylbutyraldehyde, crotonaldehyde, and aliphatic saturated or olefinically unsaturated straight or branched ketones such as:

acetone, methyl ethyl ketone, diethyl ketone, methyl n-propyl ketone, methyl isopropyl ketone, ethyl n-propyl ketone, methyl butyl ketone, ethyl isopropyl ketone, methyl isobutyl ketone, methyl sec-butyl ketone, pinacoline, di-n-propyl ketone, ethyl butyl ketone, methyl n-amyl ketone, propyl isopropyl ketone and ethyl isobutyl ketone.

The aldehydes or ketones, when used in excess, serve as solvents for the helveticoside. If the helveticoside proves to be sparingly soluble in the acetal or ketal or the corresponding aldehyde or ketone used, a solvent which is inert under the conditions of the reaction can be added, for example a lower alcohol, dioxane, tetrahydrofuran.

The process is generally carried out at temperatures between about 15° and 90°C, preferably between about

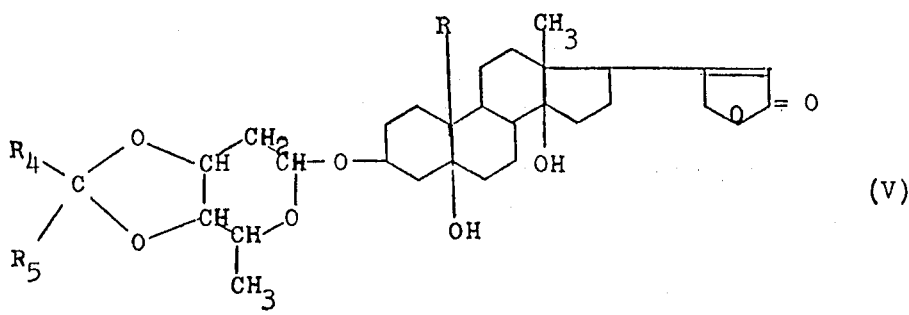

(V)

In the general formula V the R is as defined above and $R_4$ and $R_5$ can be the same or different and represent a hydrogen atom or a saturated or olefinically unsaturated, straight or branched alkyl group with 1 to 10 carbon atoms or a phenylalkyl group containing 1 to 4 carbon atoms in the alkyl moiety, the alkyl part of which can also be olefinically unsaturated or branched, or a phenyl group which may be substituted by 1 to 3 alkyl or alkoxy groups containing 1 to 4 carbon atoms or a methylenedioxy group, or $R_4$ and $R_5$ can form together with the carbon atom to which they are linked a cycloaliphatic residue containing 5 to 12 carbon atoms in the ring which may be substituted by 1 or 2 alkyl or cycloalkyl groups containing 1 to 6 carbon atoms.

In this case the starting acetal or ketal is of the general formula VI

(VI)

wherein $R_3$, $R_4$, and $R_5$ have the above meanings. Additional acetals and ketals within the scope of general 40° and 75°C. In this temperature range side-reactions are kept to a minimum. The progress of the reaction is best followed by thin-layer chromatographic analysis. Working up of the reaction mixture is commenced as soon as no more helveticoside can be detected on the thin layer chromatogram.

The working up of the reaction product is commenced, depending on the type of the condensing agent used, either after neutralizing it or after it is filtered off. Excess aldehyde or ketone or excess acetal or ketal is distilled off under reduced pressure or in high vacuum at low temperature, in order to avoid decomposition of the helveticoside. If the distillation temperatures are so high that decomposition would occur, the derivative is isolated by pouring it into low-boiling petroleum ether, whereupon the reaction product precipitates. In an analogous manner, the crystalline helveticoside derivatives are obtained by triturating the residue from the distillation with ether, petroleum ether or another hydrocarbon solvent, or the residue is dissolved in a solvent which is miscible with aliphatic hydrocarbons, such as chloroform, and then precipitated with petroleum ether.

As an alternative to precipitation with low-boiling petroluem ether, the reaction batches mixed with low-boiling petroleum ether may, if larger amounts of starting products and by-products are present, also be put into a silica gel chromatographic column using petroleum ether as solvent. By means of elution with petroleum ether the ketone or aldehyde portions of their ketals or acetals are obtained, and by subsequent elution with chloroform the corresponding helveticoside derivative is obtained.

From the cyclic acetals or ketals of the helveticoside of the general formula I wherein R denotes the formyl group obtained in this way, one can prepare the corresponding helveticosol derivatives (R = CH$_2$OH) by means of reduction. As reducing agents preferably complex metal hydrides are used which have a mild reducing activity and do not attack the lactone ring. Sodium borohydride is the preferred reducing agent. The cyclic acetal or ketal is dissolved in a water-miscible solvent, the solution is diluted with water and treated dropwise with a solution of sodium borohydride in a mixture of water and the same organic solvent. The progress of the reduction is followed by thinlayer chromatography. Dioxane and tetrahydrofuran are especially suitable as solvents. When the reduction is complete, the solvent and water are evaporated under reduced pressure and the helveticosol compounds are isolated in a manner analogous to that described above.

The first method applied is known in general preparative organic chemistry as transacetalization or transketalization. It is used specifically for the formation of acetals or ketals of sensitive carbonyl compounds. The second method is a simple acetalization or ketalization.

The preferred transacetalization method gives homogeneous products in high yields. The success of the reaction in the case of the cardioglycoside helveticoside is surprising, because apart from the two adjacent hydroxyl groups in the digitoxose part of the molecule there is a number of reactive groups which under the conditions of the reaction could react either simultaneously or preferentially.

The helveticoside used as starting material may be obtained by the procedure described in German Pat. No. 1,082,007 or German Pat. No. 1,221,764. The acetals and ketals are prepared by known methods from the corresponding aldehydes and ketones, for example by means of reaction with trialkylorthoformates.

Male and female cats, which were not fed for 18 hours prior to the test, were subjected to anesthesia with 0.8 ml./kg. i.p. of a urethane-chloralose solution (40% urethane, 8% chloralose)

Various concentrations of the derivatives to be tested were infused through the jugular vein at equal speeds. Accordingly, the so-called short-time dose at a medium lethal period of between 40 and 67 min. as well as the corresponding long-time dose at a medium lethal period of between 101 and 164 min., based on the body weight of the test animal, were determined. For this purpose, the EKG was directly recorded. If for a period of 15 sec. no EKG pattern would be observed it was established that cardiac arrest had occurred.

In order to determine the enteral resorption rates, the compounds to be tested were installed into the duodenum immediately following the laparatomy. A reflux of the solution into the stomach was prevented by previous ligature of the pylorus. 2 hours after the intraduodenal administration of the complete or half of the i.v. long-time dose the same compound were administered through the jugular vein. From the dose required to cause cardiac arrest the resorption quotient Q was determined.

$$Q = \frac{\text{i.v. lethal dose minus i.v. cardiac arrest dose}}{\text{i.d. administration}} \times 100$$

Table 1 shows the effective rates and the resorption rates ascertained by means of this method:

| Helveticoside Derivative | Effective dose DL$_{100}$ cat, mg/kg i.v. | Resorption rate % |
|---|---|---|
| Cyclopentanone-helveticoside | 0.26 | 75 |
| Cyclohexanone-helveticoside | 0.34 | 58 |
| Cyclohexanone-helveticosol | 1.01 | 55 |
| 2-Methylcyclohexanone-helveticoside | 0.39 | 65 |
| Hexylethylketone-helveticoside | 0.78 | 69 |
| 6-Methylheptene-5-one-2-helveticoside | 0.58 | 85 |
| Ethyloctylketone-helveticoside | 1.21 | 55 |
| Ethylbenzylketone-helveticoside | 0.77 | 86 |
| Benzylacetone-helveticoside | 0.47 | 73 |
| Acetophenone-helveticoside | 1.28 | 78 |
| Acetophenone-helveticosol | 0.77 | 46 |
| p-Methylacetophenone-helveticoside | 0.61 | 67 |
| p-Methylacetophenone-helveticosol | 0.87 | 62 |
| Cinnamaldehyde-helveticoside | 0.63 | 91 |

Apart from these favorable resorption values (the rate of k-strophanthin-$\beta$ is about 7%, that of helveticoside 0% and that of cymarin about 20–30%) the new compounds also have favorable elimination rates ranging between 35 and 50%. Cyclohexanonehelveticoside has, for instance, an elimination rate of 37% which compares with a rate of 7% for digitoxin, a rate of 15% for digoxin and a rate of 40% for k-strophanthin-$\beta$.

The great effectiveness, which is equal to that of the most effective glycosides used in the therapy of cardiac disease (cat, DL$_{100}$ i.v. : 0.23 mg./kg. for digoxin, 0.32–0.4 for digitoxin, 0.13 for k-strophanthin-$\beta$), the favorable resorption rate ranging between 50 and 90%, and the fast elimination make these new compounds valuable therapeutics in the treatment of cardiac insufficiency. Particularly significant are the prompt activity of these compounds in the case of peroral administration and the fast elimination as reflected in the elimination rate. In the case of an overdose the poisoning symptoms will, therefore, last for a short time only.

The invention relates to pharmaceutical preparations and their production, which contain at least one of the cardioglycosides of the general formula I. The preparations can be made for parenteral or enteral, preferably oral application by the conventional pharmaceutical process. The active ingredient content per unit dose is generally about 0.2 to 0.5 mg. Among others, the dose depends on the severity of the disease, the glycoside requirements of the individual patient and the activity of the cyclic acetal or ketal used. Usually oral preparations will be administered 2 to 4 times per day. For oral application e.g. tablets, pills, capsules or dragees can be used. The oral preparation can be coated with a stomach-resistant coating.

The basic components of tablets containing the active ingredient are e.g. corn starch, potato starch, lactose, sugar, and the like. Conventional binders employed in galenic practice, such as tragacanth, pectins, agar-agar, methyl cellulose or polyvinyl-pyrrolidone may be used. In addition, lubricating agents such as magnesium stearate, talc, and stearic acid may be used. In order to improve the disintegrating effect of starch, a high-disperse silica aero gel preparation (Aerosil[R]) is added.

Injection preparations which contain a cardioglycoside of the invention are also prepared in the usual manner. The cardioglycoside is dissolved in an aqueous solution by means of a biologically compatible solvent and the solution is adjusted to a neutral or weakly alkaline pH by means of a base. The solutions are filled into ampules sterilized by heating.

As dissolving aid for products which are insoluble in pure water e.g. ethanol, 1,2-propylene glycol or polyethylene glycols may be used. In order to adjust a pH range which insures optimum stability of the glycoside derivatives, trisodium citrate can be effectively used, apart from other buffer substances.

The following examples illustrate the processes of the invention:

EXAMPLE 1 a. Preparation of cyclohexanone-helveticoside 1.5 g. helveticoside are dissolved in 20 ml. cyclohexanone diethylketal and mixed with 1.5 g. of a cation exchanger in the $H^+$ form (e.g. the ion exchanger known by the trade name of Lewatit S 100). The mixture is heated to 55°C while stirring, and the course of the reaction is followed by thin-layer chromatography. After about 4 hours of reaction no more helveticoside can be detected. The ion exchanger is filtered off and the solvent distilled off from the filtrate in a rotating evaporator under vacuum from a water pump. The residue is triturated with petroleum ether. Yield: 850 mg. cyclohexanone-helveticoside.

The solution of cyclohexanone-helveticoside is purified on a chromatographic column (80 g. silica gel, 24 mm. diameter), using small amounts of chloroform as solvent, and extracted with chloroform. The fractions of pure cyclohexanone-helveticoside are collected and evaporated. The residue is dissolved with small amounts of chloroform and precipitated with petroleum ether. Yield: 95%, melting point: 129-134°C;[$\alpha_D^{20}$]: 34° IR bands in relation to helveticoside:

Decrease of the hydroxyl band at 3500 cm$^{-1}$; increase of the $CH_2$ band at 2925 and 1447 cm$^{-1}$ compared to the carbonyl intensities. Lactone-carbonyl bands present at 1740 and 1776 cm$^{-1}$; aldehydecarbonyl bands at 1710 cm$^{-1}$. C=C double bond bands at 1620 cm$^{-1}$.

|  |  | C | H |
|---|---|---|---|
| Analysis: | $C_{35}H_{52}O_9$: | calculated: 68.2% | 8.5% |
|  |  | found: 69.2% | 8.5% | b. Preparation of cyclohexanone-helveticosol 1.5 g. cyclohexanone-helveticoside are dissolved in 20 ml. of 80% aqueous dioxane and treated dropwise over a period of 1 hour with a solution of 0.35 g. sodium borohydride in 20 ml. of 75% dioxane. The reaction mixture is stirred for 1 hour, after which no more cyclohexanone-helveticoside can be detected. The solution is adjusted to pH 7 with dilute sulfuric acid, and the dioxane is evaporated under reduced pressure in a rotating evaporator. The aqueous phase is extracted repeatedly with chloroform. The combined chloroform extracts are dried over anhydrous sodium sulfate and evaporated. The residue is purified chromatographically over silica gel, using chloroform as solvent. Yield: 750 mg. cyclohexanone-helveticosol. Melting point: 155°-164°C;[$\alpha_D^{20}$] (C = 1, chloroform) : +23°.

EXAMPLE 2 a. Preparation of acetophenone-helveticoside 1.5 g. helveticoside are dissolved in 20 ml. acetophenone diethyl ketal and mixed with 1.5 g. of a cation exchanger in the $H^+$-form (e.g. the ion exchanger known by the trade name of Lewatit S 100). The mixture is heated to 55°C while stirring and the reaction course followed by thin-layed chromatography (silica gel, 10% methanol in chloroform as solvent). After about 4 hours of reaction no more helveticoside can be detected. The ion exchanger is filtered off and the solvent distilled off from the filtrate in a rotating evaporator under vacuum from a water pump. The residue is triturated with petroleum ether. Yield: 950 mg. acetophenone-helveticoside.

The acetophenone-helveticoside solution is purified on a chromatography column (80 g. silica gel, 24 mm. diameter), using small amounts of chloroform as solvent, and extracted with chloroform. The fractions of pure acetophenone-helveticoside are collected and evaporated. The residue is dissolved with small amounts of chloroform and precipitated with petroleum ether. Yield: 95%

Instead of distilling off the high-boiling acetophenonediethylacetal, as described above, the reaction batch can also be effectively diluted with petroleum ether at a ratio of 1:3, after removing the ion exchanger, and purified on a silica gel column (80 g. silica gel, 24 mm. diameter), notwithstanding a possible precipitate. Extraction with petroleum ether is continued until no more ketal is obtained; the mixture is then extracted with chloroform, and pure acetophenone-helveticoside is obtained. Melting point: 125-134°C (decomposition).[$\alpha_D^{20}$]: 11°.

b. Preparation of acetophenone-helveticosol 1.5 g. acetophenone-helveticoside are dissolved in 20 ml. of 80% aqueous dioxane and treated dropwise over a period of 1 hour with a solution of 0.35 g. sodium borohydride in 20 ml. of 75% dioxane. The reaction mixture is stirred for 1 hour, after which no more acetophenone-helveticoside can be detected. The solution is adjusted to pH 7 with dilute sulfuric acid, and the dioxane is removed under reduced pressure in a rotating evaporator. The aqueous phase is repeatedly extracted with chloroform. The combined chloroform extracts are dried over anhydrous sodium sulfate and evaporated. The residue is purified chromatographically over silica gel, using chloroform as solvent. Yield: 750 mg. acetophenone-helveticosol, melting point: 154°-164°C[$\alpha_D^{20}$](C = 1, chloroform): ±0°.

In the IR-spectrum, the aldehyde group can no longer be detected. However, the stronger hydroxyl band in the 3500 cm$^{-1}$ region, the lactone-carbonyl bands and the double-bond band are still present.

EXAMPLE 3 a. Preparation of benzaldehyde-helveticoside 1.5 g. helveticoside are dissolved in 20 ml. benzaldehyde diethylacetal and treated with 1.5 g. of a cation exchanger (Lewatit S 100) in the $H^+$-form. The mixture is heated to 55°C while stirring, and the course of the reaction is followed by thin-layer chromatography. After a reaction time of about 4 hours, no more helveticoside can be detected. The ion exchanger is filtered off and the solvent distilled off from the filtrate in a rotating evaporator under vacuum from a water pump. The residue is triturated with petroleum ether. Yield: 950 mg. benzaldehydehelveticoside, melting point: 202-210°C (decomposition).[$\alpha_D^{20}$] (C = 1, chloroform):+25° IR-bands: Aromatic bands at 3030, 3050, 695 and 755 cm$^{-1}$. Lactone-carbonyl bands at 1740 and 1775 cm$^{-1}$, aldehyde carbonyl band at 1719 cm$^{-1}$, C = C double-bond band at 1618 cm$^{-1}$. $\lambda$ max. 207 m$\mu$ (in $CH_3OH$).

|  |  | C | T |
|---|---|---|---|
| $C_{36}H_{48}O_9$, | calculated: | 68.2% | 8.5% |
|  | found: | 69.2% | 8.5% | b. Preparation of benzaldehyde-helveticosol 1.5 g. benzaldehyde-helveticoside are dissolved in 20 ml. of 80% aqueous dioxane and treated dropwise over a period of 1 hour with a solution of 0.35 g. sodium borohydride in 20 ml. of 75% dioxane.

The reaction mixture is stirred for 1 hour, after which no more benzaldehyde-helveticoside can be detected. The solution is adjusted to pH 7 with dilute sulfuric acid, and the dioxane evaporated under reduced pressure in a rotating evaporator. The aqueous phase is repeatedly extracted with chloroform. The combined chloroform extracts are dried over anhydrous sodium sulfate and evaporated. The residue is purified chromatographically over silica gel; chloroform is used as solvent. Yields: 750 mg. benzaldehyde-helveticosol, melting point: 167-174°C[$\alpha_D^{20}$](C = 1, chloroform): +11°.

In the IR-spectrum, the aldehyde group can no longer be detected. However, the stronger hydroxyl band in the 3500 cm$^{-1}$ region, the lactone-carbonyl bands and the double-bond band are still present.

The helveticosides enumerated in Table II were prepared in the same manner as described in Examples 1a to 3a by reacting helveticoside with the corresponding acetals or ketals.

The corresponding helveticosols were obtained in the same maner as described in Examples 1b to 3b by reduction of the helveticosides obtained.

Examples 21 to 23 illustrate the preparation of pharmaceutical compositions.

EXAMPLE 21

For producing 10,000 dragee cores each containing 0.25 mg. cyclohexanone-helveticoside and each weighing 70 mg; the following components were used:

|  | g. |
|---|---|
| lactose | 350.0 |
| corn starch | 270.0 |
| high-disperse silicic acid (Aerosil) | 35.0 |
| soluble starch | 35.0 |
| magnesium stearate | 7.5 |
| cyclohexanone-helveticoside | 2.5 |
| Total Core Weight | 700.0 |

The cardioglycoside is first mixed with a small amount of the corn starch. Subsequently the remainder of the corn starch and then the lactose are added in small increments under vigorous mixing. Subsequently Aerosil, soluble starch and magnesium stearate are admixed. The mixture is sieved through a sieve having openings of 0.25 mm and further mixed for 1 hour in a mixer. Subsequently, the mixture is granulated and the granules compressed to cores each weighing 70 mg.

Dust is removed from the cores obtained and they are coated with 40 layers of a stomach-resistant commercial resin with addition of magnesium stearate. Subsequently, the dragees are coated with a sugar-coating to reach a weight of 120 mg. each and polished in a known manner.

EXAMPLE 22

Dragee cores are prepared in the same manner as described in Example 21 containing:

|  | g. |
|---|---|
| Cyclopentanone-helveticoside | 0.0005 |
| Lactose | 0.04 |
| Dry corn starch | 0.03 |
| Aerosil | 0.003 |
| Polyvinylpyrrolidone | 0.003 |
| Talc | 0.0025 |
| Magnesium stearate | 0.001 |
| Total Core Weight: | 0.080 |

The core is coated with a stomach-resistant coating and then sugar-coated. Each dragee contains 0.5 mg. cyclopentanonehelveticoside.

Table II

| Example No. | Helveticoside-derivative | m.p. °C | $\alpha_D^{20}$* |
|---|---|---|---|
| 5a | Cyclopentanone-helveticoside | 189–192 | +28° |
| 5b | Cyclopentanone-helveticosol | 179–184 | +12° |
| 6a | cycloheptanone-helveticoside | 118–124 | +28° |
| 6b | Cycloheptanone-helveticosol | 135–141 | +23° |
| 7a | Cyclododecanone-helveticoside | 129–139 | +21° |
| 8a | 4-Methylcyclohexanone-helveticoside | 128–135 | +29° |
| 9a | 2-Methylcyclohexanone-helveticoside | 129–130 | +27° |
| 10a | Methyl decyl ketone-helveticoside | 168–178 | +28° |
| 11a | 6-Methylheptene-5-one-2-helveticoside | 186–193 | +26° |
| 12a | Ethyl hexyl ketone-helveticoside | 183–195 | +28° |
| 13a | Ethyl benzyl ketone-helveticoside | 105–112 | +16° |
| 13b | Ethyl benzyl ketone-helveticosol | 133–142 | + 5° |
| 14a | Benzylacetone-helveticoside | 105–114 | +24° |
| 14b | Benzylacetone-helveticosol | 136–144 | +11° |
| 15b | Butyrophenone-helveticosol | 120–129 | + 7° |
| 16a | 4-Methylacetophenone-helveticoside | 131–141 | + 9° |
| 16b | 4-Methylacetophenone-helveticosol | 173–183 | – 6° |
| 17a | Cinnamaldehyde-helveticoside | 129–133 | +20° |
| 17b | Cinnamaldehyde-helveticosol | 157–163 | +12° |
| 18a | Anisaldehyde-helveticoside | 103–108 | +26° |
| 18b | Anisaldehyde-helveticosol | 141–149 | +15° |
| 19a | p-Tolylaldehyde-helveticoside | 127–135 | +26° |
| 20a | Caprylaldehyde-helveticoside | 172–180 | +28° |

*Measured at C = 1 in Chloroform

EXAMPLE 23

1 ml. ampules are filled with a solution containing:

|  | mg. |
|---|---|
| Cyclopentanone-helveticoside | 0.25 |
| Ethanol (96%) | 125.0 |
| 1,2-propyleneglycol | 125.0 |
| filled up with sodium nitrate and water to 1 ml. solution of pH 7. | |

The sealed ampules are sterilized for 20 minutes under hot steam at 120°C.

We claim:
1. Cyclopentanone helveticoside.

* * * * *

UNITED STATES PATENT AND TRADEMARK OFFICE
CERTIFICATE OF CORRECTION

PATENT NO. : 3,975,373
DATED : August 17, 1976
INVENTOR(S) : Kurt H. Schmidt

It is certified that error appears in the above-identified patent and that said Letters Patent are hereby corrected as shown below:

Column 1, line 13 - correct spelling of "derived"

Column 3, line 50 - change "invention" to --inventive--

Column 3, line 61 - correct spelling of "p-isopropylbenzaldehyde"

Column 5, line 24 - insert "method" between "novel" and "is"

Column 5, line 52 - change "$R_4$ and $R_5$" to --$R_1$ and $R_2$--

Column 7, line 66 - change "were" to --was--

Column 11, line 15 - change "T" to --H--

Signed and Sealed this

Twenty-eighth Day of December 1976

[SEAL]

*Attest:*

RUTH C. MASON
*Attesting Officer*

C. MARSHALL DANN
*Commissioner of Patents and Trademarks*